United States Patent [19]

Taber et al.

[11] Patent Number: 4,689,295

[45] Date of Patent: Aug. 25, 1987

[54] TEST FOR SALMONELLA

[75] Inventors: Robert L. Taber, Wellesley; Renee A. Fitts, Framingham, both of Mass.

[73] Assignee: Integrated Genetics, Inc., Framingham, Mass.

[21] Appl. No.: 529,031

[22] Filed: Sep. 2, 1983

Related U.S. Application Data

[63] Continuation-in-part of Ser. No. 459,471, Jan. 20, 1983, abandoned.

[51] Int. Cl.⁴ .......................... C12Q 1/68; C12Q 1/02; C12N 15/00; C07H 21/00
[52] U.S. Cl. .......................................... 435/6; 935/78; 536/27; 435/253; 435/317.1; 435/34; 435/172.3; 435/879
[58] Field of Search ................ 435/6, 29, 34, 35, 253, 435/317, 172.3, 259; 436/501, 801, 803, 94, 518, 530; 536/27

[56] References Cited

U.S. PATENT DOCUMENTS

| | | | |
|---|---|---|---|
| 4,139,346 | 2/1979 | Rabbani | 422/56 |
| 4,302,204 | 11/1981 | Wahl et al. | 435/6 X |
| 4,358,535 | 11/1982 | Falkow | 435/5 |
| 4,359,535 | 11/1982 | Pjeczenik | 435/317 |
| 4,486,539 | 12/1984 | Ranki | 935/78 |

OTHER PUBLICATIONS

Stoleru, G. H. et al, *Ann. Microbiol. (Inst. Pasteur)*, vol. 127, No. 4, May–Jun., 1976, pp. 465, 477–486.
Fitts, R. et al. *Applied and Environmental Microbiology*, vol. 46, Nov. 1983, pp. 1146–1151.
Moseley, S. L. et al. *J. of Infectious Diseases*, vol. 142, No. 6, Dec. 1980, pp. 892–898.
Nichols, B. P. et al. *Proc. Nat'l Acad. Sci. USA*, vol. 76, No. 10, Oct. 1979, pp. 5244–5248.
Cleary, J. M. et al. *J. Bacteriology*, vol. 150, No. 3, Jun. 1982, pp. 1467–1471.
Stoleru, G. H., et al. *Chemical Abstracts* vol. 85, No. 13, 1976 #90053b, p. 288.
Langer, P. R. et al. *Proc. Nat'l Acad. Sci.*, vol. 78, No. 11, Nov. 1981, pp. 6633–6637.
Grunstein et al., (1975) Proc. Natl. Acad. Sci. USA 72 pp. 3961.

*Primary Examiner*—Esther M. Kepplinger
*Assistant Examiner*—Jeremy Jay

[57] ABSTRACT

Method of detecting the presence of Salmonella in a food sample including providing at least one DNA probe which is capable of selectively hybridizing to Salmonella DNA to form detectable complexes, contacting the DNA probes with the bacteria in the food sample under conditions which allow the probe to hybridize to Salmonella DNA present in the food sample to form hybrid DNA complexes, and detecting the hybrid DNA complexes as an indication of the presence of Salmonella in the food sample.

26 Claims, 2 Drawing Figures

FIG 2

Characterization Of Salmonella - Specific Cloned DNA Fragments

| Clone | Size | Restriction Map |
|---|---|---|
| RF321 | 4.9 KB | BamHI, HindIII, EcoRI, BglII, BglII, BamHI |
| RF356 | 4.1 KB | BamHI, HindIII, EcoRI, HindIII, EcoRI, BamHI |
| RF319 | 6.0 KB | BamHI, BglII, BamHI |
| RF333 | 5.7 KB | BamHI, HindIII, HindIII, BamHI |
| RF305-1 | 3.6 KB | BamHI, BglII, BglII, EcoRI, BglII, BamHI |
| RF304 | 2.3 KB | BamHI, HindIII, HindIII, BglII, BamHI, BglII |
| RF344 | 4.8 KB | BamHI, EcoRI, BamHI |
| RF347-3 | 1.4 KB | BamHI, BglII, BamHI |
| RF318 | 3.2 KB | BamHI, HindIII, BamHI |
| RF367 | 3.2 KB | BamHI, EcoRI, EcoRI, BamHI |

TEST FOR SALMONELLA

This application is a continuation-in-part of our co-pending application U.S. Ser. No. 459,471 filed Jan. 20, 1983 now abandoned.

BACKGROUND OF THE INVENTION

This invention relates to the detection of bacteria of the genus Salmonella (bacteria of the genus Salmonella refers herein to bacteria classified as such in Buchanan et al., *The Shorter Bergey's Manual for Determinative Bacteriology* (Williams & Wilkins 1982); such bacteria will be referred to hereinafter simply as "Salmonella").

The most commonly used test for the presence in food of Salmonella involves the measurement of classical biological characteristics. The test consumes several days.

SUMMARY OF THE INVENTION

In general, the invention features a method of detecting the presence of Salmonella in a food sample including providing at least one DNA probe which is capable of selectively hybridizing to Salmonella DNA to form detectable complexes, contacting the DNA probe with the bacteria in the food sample under conditions which allow the probe to hybridize to Salmonella DNA present in the food sample to form hybrid DNA complexes, and detecting the hybrid DNA complexes as an indication of the presence of Salmonella in the food sample. (The term "selectively hybridizing", as used herein, refers to a DNA probe which hybridizes only to Salmonella, and not to any other enterobacteria.)

In preferred embodiments of the invention, the probe is labeled, e.g., with a radioactive isotope, e.g. $^{32}P$ or $^{125}I$, which is incorporated into the DNA probe, e.g. by nick-translation.

In other preferred embodiments, the probe is labeled with biotin, which reacts with avidin to which is bonded a chemical entity which, when the avidin is bonded to the biotin, renders the hybrid DNA complex capable of being detected, e.g., a fluorophore, an electron-dense compound capable of rendering the hybrid DNA complexes detectable by an electron microscope, an antibody capable of rendering the hybrid DNA complexes immunologically detectable, or one of a catalyst/substrate pair capable of rendering the hybrid DNA complexes enzymatically detectable; prior to contacting the bacteria with the probe, the bacteria are lysed to release their DNA, which is then denatured and immobilized on an appropriate DNA-binding support such as a nitrocellulose membrane; and the method employs at least 2, and preferably at least 3, 4, or 5 different Salmonella-specific probes.

In other preferred embodiments, the probe is unlabeled and detection is carried out by means of sandwich hybridization.

The Salmonella detection method of the invention employs one or, preferably, more, Salmonella DNA probes, each of which is a Salmonella DNA fragment common to all or most (preferably, greater than 80%, most preferably greater than 90%) of the great number of known Salmonella species, while at the same time being apparently absent from all other enterobacteria. This finding, that there is a family of highly Salmonella-specific fragments distributed throughout the entire Salmonella genus, was extremely suprising, particularly in view of the supposed common lineage of all enterobacteria, including Salmonella.

The family of probes of the invention do not code for any protein of which we are now aware, and also are not known to contribute to pathogenicity. The method of the invention thus does not depend on the ability to match a DNA probe with any phenotypic characteristic of Salmonella; i.e., there is no need to use as a probe a DNA fragment which is known to contribute any particular distinguishing feature of the genus. As far as is known, the probes of the invention are the first bacterial genus-specific probes with such wide distribution throughout the genus.

Our discovery that there is not just one, but a number, of Salmonella-specific probes provides the added advantage of increased sensitivity and signal amplification; the larger the number of different probes used, the greater the sensitivity of the assay. This is because, when several different probes are used, each can hybridize to a different portion of a single Salmonella chromosome, so that the single chromosome bears multiple labels.

The assay of the invention gives rapid, accurate results, allowing food manufacturers to reduce food storage time prior to shipment. In addition, the short time required to complete the test permits laboratories to handle large numbers of samples in a short period of time. Furthermore, the assay, depending only on the overall DNA sequences of the bacteria rather than their biochemical properties, can detect biochemically atypical as well as typical Salmonella bacteria, so that false negatives are avoided. The test requires no elaborate equipment and can be performed easily by personnel who have not had extensive technical training.

Other features and advantages of the invention will be apparent from the following description of the preferred embodiments thereof, and from the claims.

DESCRIPTION OF THE PREFERRED EMBODIMENTS

We first briefly describe the drawings.

DRAWINGS

FIG. 2 is a table of restriction maps of Salmonella-specific probes of the invention.

FOOD SAMPLE PROCESSING APPARATUS

Figure 1:
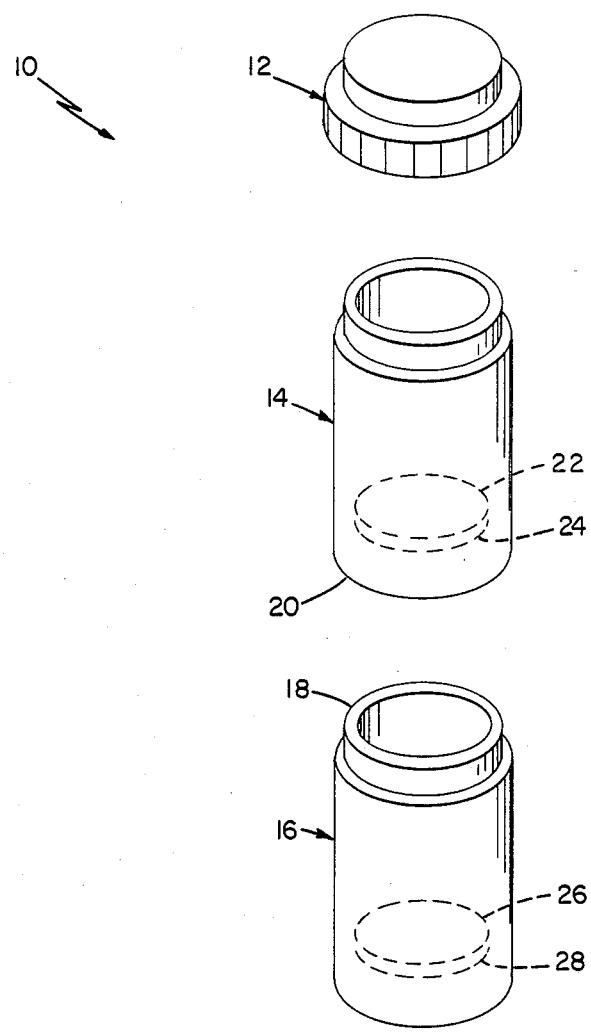
FIG. 1 is an exploded isometric view of apparatus useful in carrying out the invention.

There is shown in FIG. 1 food sample processing apparatus 10; this apparatus does not constitute a part of the present invention. The apparatus includes cap 12, top disposable cylindrical portion 14, and bottom cylindrical portion 16, the narrowed top portion 18 of which snugly mates with the recessed bottom portion of cylindrical portion 14.

Cylindrical portion 14 is fitted with large pore (5–200 micron) filter 22 capable of allowing the passage of small, Salmonella-sized bacteria while filtering out small food particles and larger bacteria. Filter 22 is supported on large-pore, rigid plastic grid 24.

Cylindrical portion 16 is fitted with nitrocellulose DNA-binding membrane 26 supported on large-pore plastic grid 28, which constitutes the floor of cylindrical portion 16. Cylindrical portion 16 is sized to fit snugly into a cylindrical hole of the manifold of a vacuum suction device (not shown).

The illustrated apparatus is employed in the method of the invention as follows. A sample of food suspected of containing Salmonella is placed in portion 14. Portions 14 and 16 are fit snugly together, and vacuum is applied at the bottom end of portion 16, causing Salmonella-sized bacteria to be deposited on filter 26, while food particles and larger bacteria remain trapped in portion 14, which is then discarded. The Salmonella detection method of the invention is then carried out on the bacteria on filter 26, as will be described in detail below.

DNA Probes

A library of *S. typhimurium* DNA is constructed using the plasmid vector YEp13, described in Broach et al. (1979) Gene 8, 121. DNA from *S. typhimurium*, strain ATCC e23566 is digested to completion with the restriction endonuclease Bam HI to create fragments of varying lengths, and is then ligated into the unique Bam HI site of YEp13, using the general method described in Cohen et al. (1973) PNAS 70, 3240. This ligation mix is then used to transform either a Leu⁻ *Saccharomyces cereviseae* (yeast) host, or a culture of *E. coli* strain MC1061; *E. coli* transformants are selected on the basis of ampicillin resistance. The yeast and *E. coli* host cells are amplified in a 500 ml volume to yield the Salmonella DNA library. The library of *Salmonella typhimurium* DNA is then screened in order to isolate restriction enzyme digestion fragments which hybridize selectively with Salmonella DNA but do not cross-hybridize with the DNAs of other bacteria found in food, including other bacteria in the family Enterobacteriaceae (herein, "enterabacteria"). Screening is carried out with genomic *S. typhimurium* or *E. coli* DNA nick-translated with a radioactive isotope.

The above screening procedure in yeast yields a fragment which selectively hybridizes to Salmonella DNA and not to other bacteria, including other enterobacteria. The *E. coli* clone containing plasmid YEp13 bearing this fragment was deposited in the culture collection of the American Type Culture Collection in Rockville, Md. on Jan. 10, 1983 identified there as RF 305, and assigned ATCC accession number 39261.

To verify that the above fragment is common to a variety of Salmonella cultures, this fragment is cut out of the plasmid vector with Bam HI, purified by agarose gel electrophoresis, nick-translated with 32$p$ using the nick-translation method described in Rigby et al. (1977) J. Mol. Biol. 113, 237, and screened, in single-stranded form, against the DNAs of a number of field isolates of Salmonella. The fragment is found to hybridize with all of the field isolates tested.

Additional Salmonella specific probes are obtained as described above, screening about 200 plasmid minipreps from *E. coli* MC1061, rather than yeast. In more detail, the method is as follows.

First, plasmid minipreps of MC1061 transformants are prepared, by the method of Holmes et al. (1981) Anal. Biochem 114, 193. Restriction enzyme digests of these minipreps are electrophoresed through agarose gels and transferred to nitrocellulose filters, as described in Southern (1975), J. mol. Biol. 98, 503. Genomic DNA from strain MC1061, nick-translated with alpha-(32-P)dATP or alpha-(32-P)dCTP, is used in hybridizations with these filters, as described in Denhardt (1966) B.B.R.C. 23, 641. Washes after hybridization are performed at 65 degrees C. with 0.3 M NaCl/0.03M sodium citrate for 30 minutes. Those clones containing fragments of Salmonella DNA which do not hybridize to the *E. coli* probe are further screened against a variety of Salmonella and non-Salmonella strains to verify the specificity of these sequences for Salmonella.

A total of 54 cloned fragments that appear not to hybridize to the *E. coli* probe are obtained from the plasmid collection examined by minipreps. These clones are then screened against 23 Salmonella cultures and 32 non-Salmonella cultures listed in Table 1, below. Salmonella strains (including all arizonae) mentioned herein are described by the conventions of *The Shorter Bergey's Manual of Determinative Bacteriology*, Id, such that each serotype is given a species name. When only the serotype and not its corresponding species name is known, the serotype is given. With the exception of strains serotyped by the Centers for Disease Control (CDC), Atlanta, Ga., all strains are tested for H antigen specificity using the Spicer-Edwards system (Difco; Spratt et al., Mol. Gen. 121:347–353).

Salmonella isolates mentioned herein are summarized by 0 antigen groups in Table 2 below; those isolates of specific interest are described in Table 1. Non-Salmonella strains, where noted, are isolated from foods and identified using the Enteric-tek identification system (Difco) with tests of growth parameters on a variety of other bacteriological media. In some of these instances, only the genus is indicated.

TABLE 1

| Strain | Bacterial and Yeast Strains Description | Source |
|---|---|---|
| e23566 | *S. typhimurium* LT2 (P22) + | ATCC |
| MC1061 | *E. coli* | |
| XY820-4A | *S. cereviseae* leu2-3 leu2-12 can1-11 ade2-G10 | |
| DB9000 | *S. typhimurium* pyrF146 amtA trp130 his57 zee629::Tn5 (fels-, plasmid-) | |
| S100 | Salmonella B(0):Z29(H) | a |
| S102 | Salmonella G(0):Z29(H) | a |
| S104 | Salmonella Cl(0):G complex(H) | a |
| S105 | Salmonella M(0):Z10 + encomplex(H) | a |
| S106 | Salmonella F(0):en complex(H) | a |
| S108 | Salmonella Cl(0):r + complex(H) | a |
| S110 | Salmonella K(0):Z4(H) | a |
| S111 | Salmonella Cl(0):Z29(H) | a |
| S124 | Salmonella E2(0):i(H) | a |
| S125 | Salmonella M(0):Z10(H) | a |
| S126 | Salmonella F(0):K + 1 complex(H) | a |
| S127 | Salmonella O(0):Z4(H) | a |
| S128 | Salmonella G(0):G complex(H) | a |
| S129 | Salmonella B(0):i(H) | a |
| S130 | Salmonella E2(0):en complex(H) | a |
| S131 | Salmonella I(0):b(H) | a |
| S132 | Salmonella G(0):Z + en complex(H) | a |
| SA19 | *S. newport* | a |
| SA20 | *S. bredeney* | a |
| SA21 | *S. thompson* | a |
| SA22 | *S. infantis* | a |

TABLE 1-continued

Bacterial and Yeast Strains

| Strain | Description | Source |
|---|---|---|
| SA24 | S. javiana | a |
| S103A | Klebsiella | b |
| S103B | Citrobacter | b |
| S107 | Enterobacter | b |
| S109A | Enterobacter | b |
| S109B | Enterobacter | b |
| S115A | Enterobacter | b |
| S115B | Proteus vulgaris | b |
| S117A | Klebsiella | b |
| S117B | Proteus vulgaris | b |
| S118A | Citrobacter freundi | b |
| S118B | Proteus vulgaris | b |
| S112 | Enterobacter | b |
| S113 | Citrobacter | b |
| S114 | Citrobacter | b |
| S116 | Citrobacter | b |
| S133 | Proteus vulgaris | a |
| S134 | Enterobacter cloacae | a |
| S135 | Citrobacter freundii | a |
| RF875 | S. treforest | c |
| RF876 | S. utrecht | c |
| RF877 | S. humbar | c |
| RF878 | S. uccle | c |
| RF879 | S. tranora | c |
| RF880 | S. artis | c |
| RF882 | S. tokai | c |
| RF883 | S. basel | c |
| RF884 | S. betioky | c |
| RF885 | S. luton | c |
| RF886 | Salmonella (64:k;e,n,x,z15) | c |
| RF887 | Salmonella (65:-:1,6) | c |
| RF888 | S. brookfield | c |
| RF889 | S. crossness | c |
| RF890 | S. brookfield | c |
| RF891 | Salmonella (66:z35:-) | c |
| RF892 | S. bangor | c |
| RF893 | Salmonella (66:z65:-) | c |
| RF894 | Salmonella (48:z41:-) | c |
| RF895 | Salmonella (44:4:-) | c |
| RF896 | S. simsbury | c |
| RF897 | S. rutgers | c |
| RF898 | S. aesch | c |
| RF899 | S. crossness | c |
| RF900 | S. anarctica | c |
| RF901 | S. kunzendorf | c |
| RF943 | Shigella flexneri | d |
| RF944 | Shigella (Group B) | d |
| RF945 | S. flexneri | d |
| RF946 | Shigella (Group B) | d |
| RF947 | Shigella (Group B) | d |
| RF948 | Shigella (Group C) | d |
| RF949 | Shigella (Group D) | d |
| RF950 | Shigella (Group B) | d |
| RF951 | Shigella (Group B) | d |
| RF952 | Shigella (Group A) | d |
| RF953 | Yersinia enterocolitica | d |
| RF954 | Y. enterocolitica | d |
| RF955 | Y. enterocolitica | d | a Silliker Laboratories
b this work
c Center for Disease Control
d Gary Doern

Most of the 54 clones not hybridizing to E. coli do cross-hybridize to some of the non-Salmonella cultures, including the ten clones illustrated in FIG. 2, are found to be highly specific for the Salmonella cultures, with no cross-hybridization to other isolates. These are then extensively studied by using the cloned inserts in each as probes to survey other Salmonella isolates.

This screening is carried out as follows. First, the fourteen Salmonella-specific fragments are cut out of the plasmid vector using Bam HI, electrophoresed through agarose gels, electroeluted, and labeled with $^{32}P$ via nick-translation, as described above.

Dot blots of Salmonella and other bacterial isolates to be surveyed using the above probes are prepared by concentrating cultures of the bacteria in L broth approximately 20-fold and then spotting one-microliter drops onto nitrocellulose filters. The bacteria are lysed in situ and their DNAs denatured and fixed by placing filters sequentially onto Whatman 3M paper saturated with 0.2M NaOH/ 0.6M NaCl and 1M Tris (pH 8.0)/0.6M NaCl, and then immersing the filters in absolute ethanol and allowing them to dry.

The results of the above screening procedure are given in Table 2, below. As shown therein, clone RF321 (FIG. 2) hybridizes to every Salmonella isolate tested.

TABLE 2

DISTRIBUTION OF SALMONELLA-SPECIFIC SEQUENCES WITHIN THE GENUS SALMONELLA

| Species or Serotype | Number of isolates tested | NUMBER OF ISOLATES HYBRIDIZED WITH | | | | | | | | |
|---|---|---|---|---|---|---|---|---|---|---|
| | | RF321 | RF356 | RF319 | RF333 | RF305-1 | RF304 | RF344 | RF318 | RF347-3 | RF367 |
| Group A | | | | | | | | | | | |
| S. paratyphi A | 5 | 5 | 5 | 5 | 5 | 5 | 1 | 0 | 0 | 0 | 1 |
| Group B | | | | | | | | | | | |
| Salmonella (4,5,12:z6,-) | 1 | 1 | 1 | 1 | 1 | 1 | 0 | 0 | 1 | 1 | 0 |
| (4,12:3,n:z15) | 1 | 1 | 1 | 1 | 1 | 1 | 0 | 0 | 0 | 0 | 0 |
| S. abortus-equi | 1 | 1 | 1 | 1 | 1 | 1 | 0 | 0 | 1 | 1 | 0 |
| S. abortus-ovis | 2 | 2 | 2 | 2 | 2 | 1 | 0 | 0 | 0 | 0 | 0 |
| S. agona | 3 | 3 | 3 | 3 | 3 | 3 | 0 | 3 | 2 | 2 | 0 |
| S. bispebjerg | 1 | 1 | 1 | 1 | 1 | 1 | 0 | 0 | 1 | 1 | 0 |
| S. brandenburg | 1 | 1 | 1 | 1 | 1 | 1 | 0 | 0 | 1 | 1 | 0 |
| S. bredeney | 3 | 3 | 3 | 3 | 3 | 3 | 0 | 2 | 1 | 1 | 0 |
| S. budapest | 1 | 1 | 1 | 1 | 1 | 1 | 0 | 1 | 1 | 1 | 0 |
| S. chester | 1 | 1 | 1 | 1 | 1 | 1 | 0 | 0 | 0 | 0 | 0 |
| S. derby | 4 | 4 | 4 | 4 | 4 | 4 | 0 | 0 | 4 | 4 | 0 |
| S. essen | 1 | 1 | 1 | 1 | 1 | 1 | 0 | 0 | 0 | 0 | 0 |
| S. heidelberg | 4 | 4 | 4 | 4 | 4 | 4 | 4 | 0 | 4 | 4 | 0 |
| S. java | 3 | 3 | 3 | 3 | 3 | 3 | 0 | 2 | 3 | 3 | 0 |
| S. paratyphi B | 7 | 7 | 7 | 7 | 7 | 7 | 0 | 5 | 6 | 6 | 0 |
| S. reading | 2 | 2 | 2 | 2 | 2 | 2 | 0 | 0 | 0 | 0 | 0 |

TABLE 2-continued

DISTRIBUTION OF SALMONELLA-SPECIFIC SEQUENCES WITHIN THE GENUS SALMONELLA

| Species or Serotype | Number of isolates tested | NUMBER OF ISOLATES HYBRIDIZED WITH | | | | | | | | | |
|---|---|---|---|---|---|---|---|---|---|---|---|
| | | RF321 | RF356 | RF319 | RF333 | RF305-1 | RF304 | RF344 | RF318 | RF347-3 | RF367 |
| S. st. paul | 3 | 3 | 3 | 3 | 3 | 3 | 0 | 0 | 3 | 3 | 0 |
| S. san-diego | 1 | 1 | 1 | 1 | 1 | 1 | 0 | 0 | 0 | 0 | 0 |
| S. schleissheim | 1 | 1 | 1 | 1 | 1 | 1 | 0 | 0 | 0 | 0 | 0 |
| S. stanley | 1 | 1 | 1 | 1 | 1 | 1 | 0 | 1 | 0 | 0 | 0 |
| S. typhimurium | 13 | 13 | 13 | 13 | 13 | 13 | 13 | 13 | 13 | 13 | 9 |
| Group C1 | | | | | | | | | | | |
| S. amersfoort | 1 | 1 | 1 | 1 | 1 | 1 | 0 | 0 | 1 | 1 | 0 |
| S. bareilly | 2 | 2 | 2 | 2 | 2 | 2 | 0 | 0 | 2 | 2 | 2 |
| S. braenderup | 4 | 4 | 4 | 4 | 4 | 4 | 0 | 0 | 4 | 4 | 4 |
| S. cholerae-suis | 6 | 6 | 6 | 6 | 6 | 6 | 0 | 0 | 6 | 6 | 4 |
| S. hartford | 1 | 1 | 1 | 1 | 1 | 1 | 0 | 0 | 1 | 1 | 0 |
| S. infantis | 5 | 5 | 5 | 5 | 5 | 5 | 0 | 0 | 4 | 4 | 0 |
| S. livingston | 1 | 1 | 1 | 1 | 1 | 1 | 1 | 1 | 1 | 1 | 0 |
| S. mbandaka | 1 | 1 | 1 | 1 | 1 | 1 | 0 | 0 | 0 | 0 | 0 |
| S. mikawasima | 2 | 2 | 2 | 2 | 2 | 2 | 0 | 0 | 2 | 2 | 0 |
| S. montevideo | 4 | 4 | 4 | 4 | 4 | 4 | 1 | 2 | 0 | 0 | 0 |
| S. ohio | 1 | 1 | 1 | 1 | 1 | 1 | 0 | 1 | 1 | 1 | 0 |
| S. oranienberg | 4 | 4 | 4 | 4 | 4 | 4 | 0 | 0 | 0 | 0 | 1 |
| S. oslo | 1 | 1 | 1 | 1 | 1 | 1 | 0 | 0 | 1 | 1 | 0 |
| S. paratyphi C | 1 | 1 | 1 | 1 | 1 | 1 | 0 | 0 | 1 | 1 | 0 |
| S. potsdam | 1 | 1 | 1 | 1 | 1 | 1 | 0 | 0 | 1 | 1 | 0 |
| S. tennesse | 2 | 2 | 2 | 2 | 2 | 2 | 0 | 0 | 0 | 0 | 0 |
| S. thompson | 6 | 6 | 6 | 6 | 6 | 6 | 0 | 0 | 5 | 5 | 0 |
| S. thphi-suis | 1 | 1 | 1 | 1 | 1 | 1 | 0 | 0 | 1 | 1 | 0 |
| S. virchow | 2 | 2 | 2 | 2 | 2 | 2 | 0 | 0 | 1 | 1 | 0 |
| Group C2 | | | | | | | | | | | |
| S. blockley | 4 | 4 | 4 | 4 | 4 | 4 | 0 | 0 | 4 | 4 | 1 |
| S. bovismorbificans | 1 | 1 | 1 | 1 | 1 | 1 | 0 | 0 | 1 | 1 | 0 |
| S. dusseldorf | 1 | 1 | 1 | 1 | 1 | 1 | 0 | 0 | 0 | 0 | 0 |
| S. glostrup | 1 | 1 | 1 | 1 | 1 | 1 | 0 | 0 | 0 | 0 | 0 |
| S. haardt | 2 | 2 | 2 | 2 | 2 | 2 | 0 | 0 | 1 | 1 | 0 |
| S. kottbus | 1 | 1 | 1 | 1 | 1 | 1 | 0 | 0 | 1 | 1 | 0 |
| S. litchfield | 1 | 1 | 1 | 1 | 1 | 1 | 0 | 0 | 1 | 1 | 0 |
| S. mandaka | 1 | 1 | 1 | 1 | 1 | 1 | 0 | 0 | 0 | 0 | 0 |
| S. muenchen | 4 | 4 | 4 | 4 | 4 | 1 | 0 | 0 | 4 | 4 | 0 |
| S. narashino | 1 | 1 | 1 | 1 | 1 | 1 | 0 | 0 | 1 | 1 | 0 |
| S. newport | 6 | 6 | 6 | 6 | 6 | 1 | 0 | 1 | 6 | 6 | 0 |
| S. tallahassee | 1 | 1 | 1 | 1 | 1 | 1 | 0 | 0 | 1 | 1 | 0 |
| S. tulear | 1 | 1 | 1 | 1 | 1 | 1 | 0 | 0 | 0 | 0 | 0 |
| Group C3 | | | | | | | | | | | |
| S. kentucky | 1 | 1 | 1 | 1 | 1 | 1 | 0 | 0 | 1 | 1 | 0 |
| S. virginia | 1 | 1 | 1 | 1 | 1 | 1 | 0 | 0 | 1 | 1 | 0 |
| S. bornum | 1 | 1 | 1 | 1 | 1 | 1 | 0 | 0 | 0 | 0 | 0 |
| Group D | | | | | | | | | | | |
| S. berta | 1 | 1 | 1 | 1 | 1 | 1 | 0 | 0 | 1 | 1 | 0 |
| S. glegdam | 1 | 1 | 1 | 1 | 1 | 1 | 0 | 0 | 1 | 1 | 0 |
| S. dar-es-saalam | 1 | 1 | 1 | 1 | 1 | 1 | 0 | 0 | 1 | 1 | 0 |
| S. dublin | 1 | 1 | 1 | 1 | 1 | 1 | 0 | 0 | 1 | 1 | 0 |
| S. eastbourne | 1 | 1 | 1 | 1 | 1 | 1 | 1 | 1 | 0 | 0 | 0 |
| S. enteritidis | 4 | 4 | 4 | 4 | 4 | 4 | 0 | 0 | 4 | 4 | 4 |
| S. gallinarum | 1 | 1 | 1 | 1 | 1 | 1 | 0 | 0 | 1 | 1 | 0 |
| S. javiana | 3 | 3 | 3 | 3 | 3 | 3 | 1 | 3 | 2 | 2 | 0 |
| S. moscow | 1 | 1 | 1 | 1 | 1 | 1 | 0 | 0 | 1 | 1 | 1 |
| S. napoli | 1 | 1 | 1 | 1 | 1 | 1 | 0 | 1 | 1 | 1 | 0 |
| S. panama | 4 | 4 | 4 | 4 | 4 | 4 | 0 | 0 | 0 | 0 | 0 |
| S. pensacola | 1 | 1 | 1 | 1 | 1 | 1 | 0 | 0 | 1 | 1 | 0 |
| S. rostock | 1 | 1 | 1 | 1 | 1 | 1 | 0 | 0 | 1 | 1 | 1 |
| S. sendai | 1 | 1 | 1 | 1 | 1 | 1 | 0 | 0 | 0 | 0 | 0 |
| S. typhi | 7 | 7 | 7 | 7 | 7 | 7 | 0 | 0 | 0 | 0 | 0 |
| S. fresno | 1 | 1 | 1 | 1 | 1 | 1 | 0 | 0 | 0 | 0 | 0 |
| S. gateshead | 1 | 1 | 1 | 1 | 1 | 1 | 0 | 1 | 0 | 0 | 0 |
| S. strasbourg | 1 | 1 | 1 | 1 | 1 | 1 | 0 | 0 | 1 | 1 | 0 |
| Group E | | | | | | | | | | | |
| Salmonella (3,10:1,6:-) | 1 | 1 | 1 | 1 | 1 | 1 | 0 | 0 | 1 | 1 | 0 |
| S. anatum | 4 | 4 | 4 | 4 | 4 | 4 | 0 | 0 | 4 | 4 | 0 |
| S. butantan | 1 | 1 | 1 | 1 | 1 | 1 | 0 | 1 | 0 | 0 | 0 |
| S. give | 1 | 1 | 1 | 1 | 1 | 1 | 0 | 1 | 0 | 0 | 0 |
| S. london | 2 | 2 | 2 | 2 | 2 | 2 | 0 | 2 | 0 | 0 | 0 |
| S. meleagridis | 1 | 1 | 1 | 1 | 1 | 1 | 0 | 0 | 0 | 0 | 0 |
| S. muenster | 2 | 2 | 2 | 2 | 2 | 2 | 0 | 2 | 0 | 0 | 0 |
| S. nyborg | 1 | 1 | 1 | 1 | 1 | 1 | 0 | 1 | 0 | 0 | 0 |
| S. orion | 1 | 1 | 1 | 1 | 1 | 1 | 0 | 0 | 1 | 1 | 0 |
| S. pullorum | 1 | 1 | 1 | 1 | 1 | 1 | 0 | 0 | 1 | 1 | 0 |
| S. arkansas | 1 | 1 | 1 | 1 | 1 | 1 | 0 | 1 | 1 | 1 | 0 |
| S. newington | 1 | 1 | 1 | 1 | 1 | 1 | 0 | 0 | 1 | 1 | 0 |

TABLE 2-continued

DISTRIBUTION OF SALMONELLA-SPECIFIC SEQUENCES WITHIN THE GENUS SALMONELLA

| Species or Serotype | Number of isolates tested | NUMBER OF ISOLATES HYBRIDIZED WITH | | | | | | | | | |
|---|---|---|---|---|---|---|---|---|---|---|---|
| | | RF321 | RF356 | RF319 | RF333 | RF305-1 | RF304 | RF344 | RF318 | RF347-3 | RF367 |
| S. illinois | 2 | 2 | 2 | 2 | 2 | 2 | 0 | 0 | 2 | 2 | 0 |
| S. menneapolis | 1 | 1 | 1 | 1 | 1 | 1 | 0 | 0 | 1 | 1 | 0 |
| S. new brunswick | 3 | 3 | 3 | 3 | 3 | 0 | 3 | 3 | 3 | 3 | 0 |
| S. chittagong | 1 | 1 | 1 | 1 | 1 | 1 | 0 | 0 | 1 | 1 | 0 |
| S. krefeld | 1 | 1 | 1 | 1 | 1 | 1 | 1 | 1 | 1 | 1 | 0 |
| S. luciana | 1 | 1 | 1 | 1 | 1 | 1 | 0 | 1 | 1 | 1 | 0 |
| S. seftenberg | 2 | 2 | 2 | 2 | 2 | 2 | 0 | 0 | 2 | 2 | 0 |
| S. westerstede | 1 | 1 | 1 | 1 | 1 | 1 | 0 | 0 | 1 | 1 | 0 |
| Groups F,G | | | | | | | | | | | |
| S. aberdeen | 1 | 1 | 1 | 1 | 1 | 1 | 0 | 0 | 1 | 1 | 0 |
| S. rubislaw | 2 | 2 | 2 | 2 | 2 | 2 | 0 | 2 | 2 | 2 | 0 |
| S. marshall | 1 | 1 | 1 | 1 | 1 | 1 | 0 | 0 | 0 | 0 | 0 |
| S. poona | 3 | 3 | 3 | 3 | 3 | 3 | 3 | 3 | 0 | 0 | 0 |
| S. havana | 1 | 1 | 1 | 1 | 1 | 1 | 0 | 0 | 1 | 1 | 0 |
| S. mississippi | 1 | 1 | 1 | 1 | 1 | 1 | 0 | 1 | 0 | 0 | 0 |
| S. wichita | 1 | 1 | 1 | 1 | 1 | 1 | 0 | 0 | 1 | 1 | 0 |
| S. worthington | 2 | 2 | 2 | 2 | 2 | 2 | 0 | 0 | 0 | 0 | 0 |
| Groups H, I, J, | | | | | | | | | | | |
| S. boecker | 1 | 1 | 1 | 1 | 1 | 1 | 0 | 1 | 0 | 0 | 0 |
| S. carrau | 1 | 1 | 1 | 1 | 1 | 1 | 1 | 1 | 0 | 0 | 0 |
| S. onderstepoort | 1 | 1 | 1 | 1 | 1 | 1 | 0 | 1 | 0 | 0 | 0 |
| S. florida | 1 | 1 | 1 | 1 | 1 | 1 | 1 | 1 | 0 | 0 | 0 |
| S. horsham | 1 | 1 | 1 | 1 | 1 | 1 | 0 | 1 | 0 | 0 | 0 |
| S. sundsvall | 1 | 1 | 1 | 1 | 1 | 1 | 1 | 1 | 0 | 0 | 0 |
| S. gaminara | 1 | 1 | 1 | 1 | 1 | 1 | 0 | 0 | 0 | 0 | 0 |
| S. nottingham | 1 | 1 | 1 | 1 | 1 | 1 | 0 | 1 | 0 | 0 | 0 |
| S. kirkee | 1 | 1 | 1 | 1 | 1 | 1 | 0 | 1 | 1 | 1 | 0 |
| S. cerro | 5 | 5 | 5 | 5 | 5 | 5 | 3 | 1 | 4 | 4 | 0 |
| Groups L, M, N | | | | | | | | | | | |
| S. minnesota | 2 | 2 | 2 | 2 | 2 | 2 | 0 | 2 | 0 | 0 | 0 |
| Salmonella (28:y:-) | 1 | 1 | 1 | 1 | 1 | 1 | 0 | 0 | 0 | 0 | 0 |
| S. babelsberg | 1 | 1 | 1 | 1 | 1 | 1 | 0 | 0 | 0 | 0 | 0 |
| S. dakar | 1 | 1 | 1 | 1 | 1 | 1 | 0 | 1 | 0 | 0 | 0 |
| S. pomona | 1 | 1 | 1 | 1 | 1 | 1 | 0 | 0 | 0 | 0 | 0 |
| S. matopeni | 1 | 1 | 1 | 1 | 1 | 1 | 0 | 0 | 0 | 0 | 0 |
| S. morehead | 1 | 1 | 1 | 1 | 1 | 1 | 0 | 0 | 0 | 0 | 0 |
| S. ramat-gan | 1 | 1 | 1 | 1 | 1 | 1 | 1 | 1 | 1 | 1 | 0 |
| S. soerenga | 1 | 1 | 1 | 1 | 1 | 1 | 0 | 1 | 1 | 1 | 0 |
| S. sternschanze | 1 | 1 | 1 | 1 | 1 | 1 | 0 | 0 | 0 | 0 | 0 |
| S. urbana | 2 | 2 | 2 | 2 | 2 | 2 | 0 | 0 | 0 | 0 | 0 |
| S. wayne | 1 | 1 | 1 | 1 | 1 | 1 | 0 | 0 | 0 | 0 | 0 |
| Groups O, P, Q | | | | | | | | | | | |
| S. adelaide | 2 | 2 | 2 | 2 | 2 | 2 | 0 | 0 | 2 | 2 | 0 |
| S. alachua | 1 | 1 | 1 | 1 | 1 | 1 | | 1 | 1 | 1 | 0 |
| S. monshaui | 2 | 2 | 2 | 2 | 2 | 2 | 0 | 2 | 2 | 2 | 0 |
| S. emmastad | 1 | 1 | 1 | 1 | 1 | 1 | 0 | 0 | 1 | 1 | 1 |
| S. freetown | 1 | 1 | 1 | 1 | 1 | 1 | 0 | 0 | 0 | 0 | 0 |
| S. inverness | 2 | 2 | 2 | 2 | 2 | 2 | 0 | 2 | 0 | 0 | 0 |
| S. lansing | 1 | 1 | 1 | 1 | 1 | 1 | 0 | 0 | 1 | 1 | 0 |
| S. champaign | 2 | 2 | 2 | 2 | 2 | 2 | 0 | 2 | 2 | 2 | 0 |
| Groups R, S, T | | | | | | | | | | | |
| S. bern | 1 | 1 | 1 | 1 | 1 | 1 | 0 | 0 | 0 | 0 | 1 |
| S. bulawayo | 1 | 1 | 1 | 1 | 1 | 1 | 0 | 0 | 0 | 0 | 0 |
| S. johannesburg | 1 | 1 | 1 | 1 | 1 | 1 | 0 | 0 | 1 | 1 | 0 |
| S. karamoja | 1 | 1 | 1 | 1 | 1 | 1 | 0 | 1 | 0 | 0 | 0 |
| S. riogrande | 1 | 1 | 1 | 1 | 1 | 1 | 0 | 0 | 0 | 0 | 0 |
| S. springs | 1 | 1 | 1 | 1 | 1 | 1 | 0 | 1 | 1 | 1 | 0 |
| S. waycross | 1 | 1 | 1 | 1 | 1 | 1 | 0 | 0 | 0 | 0 | 0 |
| S. weslaco | 2 | 2 | 0 | 2 | 2 | 2 | 0 | 0 | 0 | 0 | 0 |
| Groups U, V, W | | | | | | | | | | | |
| S. berkeley | 1 | 1 | 1 | 1 | 1 | 1 | 0 | 0 | 1 | 1 | 0 |
| S. bunnik | 2 | 2 | 2 | 2 | 2 | 2 | 0 | 0 | 2 | 2 | 0 |
| S. kingabwa | 2 | 2 | 2 | 2 | 2 | 2 | 0 | 0 | 2 | 2 | 0 |
| S. guinea | 1 | 1 | 1 | 1 | 1 | 1 | 0 | 0 | 0 | 0 | 0 |
| S. niarembe | 1 | 1 | 1 | 1 | 1 | 1 | 0 | 1 | 0 | 0 | 0 |
| S. deversoir | 1 | 1 | 1 | 1 | 1 | 1 | 0 | 0 | 0 | 0 | 0 |
| S. dugbe | 1 | 1 | 1 | 1 | 1 | 1 | 0 | 1 | 0 | 0 | 0 |
| Groups X, Y, Z | | | | | | | | | | | |
| S. bere | 1 | 1 | 1 | 1 | 1 | 1 | 0 | 1 | 1 | 1 | 0 |
| S. bergen | 1 | 1 | 1 | 1 | 1 | 1 | 1 | 1 | 0 | 0 | 0 |
| S. kaolack | 1 | 1 | 1 | 1 | 1 | 1 | 0 | 0 | 0 | 0 | 0 |
| S. quimbamba | 1 | 1 | 1 | 1 | 1 | 1 | | 1 | 0 | 0 | 0 |
| S. quinhon | 1 | 1 | 0 | 1 | 1 | 1 | 0 | | 0 | 0 | 0 |
| S. dahlem | 1 | 1 | 1 | 1 | 1 | | 0 | 1 | 0 | 0 | 0 |
| S. djakarta | 1 | 1 | 1 | 1 | 1 | 1 | 0 | 0 | 0 | 0 | 0 |

TABLE 2-continued

DISTRIBUTION OF SALMONELLA-SPECIFIC SEQUENCES WITHIN THE GENUS SALMONELLA

| Species or Serotype | Number of isolates tested | NUMBER OF ISOLATES HYBRIDIZED WITH | | | | | | | | | |
|---|---|---|---|---|---|---|---|---|---|---|---|
| | | RF321 | RF356 | RF319 | RF333 | RF305-1 | RF304 | RF344 | RF318 | RF347-3 | RF367 |
| S. flint | 1 | 1 | 1 | 1 | 1 | 1 | 0 | 0 | 0 | 0 | 0 |
| S. greenside | 1 | 1 | 1 | 1 | 1 | 1 | 0 | 0 | 0 | 0 | 0 |
| S. hooggraven | 1 | 1 | 1 | 1 | 1 | 0 | 0 | 0 | 0 | 0 | 0 |
| S. wassenaar | 2 | 2 * | 2 | 2 | 2 | 0 | 0 | 0 | 0 | 0 | 0 |
| Higher O Groups | | | | | | | | | | | |
| S. treforest | 1 | 1 | 1 | 1 | 1 | 1 | 0 | 1 | 0 | 0 | 0 |
| S. utrecht | 1 | 1 | 1 | 1 | 1 | 1 | 0 | 0 | 1 | 1 | 0 |
| S. humber | 1 | 1 | 1 | 1 | 1 | 1 | 0 | 1 | 0 | 0 | 0 |
| S. uccle | 1 | 1 | 0 | 1 | 1 | 1 | 0 | 0 | 1 | 1 | 0 |
| S. tranoroa | 1 | 1 | 1 | 1 | 1 | 1 | 0 | 0 | 0 | 0 | 0 |
| S. artis | 1 | 1 | 1 | 1 | 1 | 1 | 0 | 1 | 0 | 0 | 0 |
| S. tokai | 1 | 1 | 1 | 1 | 1 | 0 | 1 | 0 | 0 | 0 | 0 |
| S. basel | 1 | 1 | 1 | 1 | 1 | 1 | 0 | 0 | 0 | 0 | 0 |
| S. betioky | 1 | 1 | 1 | 1 | 1 | 1 | 0 | 0 | 0 | 0 | 0 |
| S. luton | 1 | 1 | 1 | 1 | 1 | 1 | 0 | 0 | 0 | 0 | 0 |
| S. brookfield | 2 | 2 | 2 | 2 | 0 | 0 | 0 | 1 | 0 | 0 | 0 |
| S. crossness | 1 | 1 | 1 | 1 | 1 | 1 | 0 | 0 | 1 | 1 | 0 |
| S. bangor | 1 | 1 | 1 | 1 | 0 | 0 | 0 | 0 | 0 | 0 | 0 |
| S. simsbury | 1 | 1 | 1 | 1 | 1 | 1 | 0 | 0 | 0 | 0 | 0 |
| Salmonella | | | | | | | | | | | |
| (64:k:3,n,x,z15) | 1 | 1 | 1 | 1 | 1 | 0 | 0 | 1 | 0 | 0 | 0 |
| (65:-:1,6) | 1 | 1 | 1 | 1 | 1 | 1 | 0 | 0 | 0 | 0 | 0 |
| (66:z35:-) | 1 | 1 | 1 | 1 | 1 | 0 | 0 | 0 | 0 | 0 | 0 |
| (66:z65:-) | 1 | 1 | 1 | 1 | 1 | 0 | 0 | 1 | 0 | 0 | 0 |
| (48:z41:-) | 1 | 1 | 1 | 1 | 1 | 0 | 0 | 0 | 0 | 0 | 0 |
| (44:4:-) | 1 | 1 | 1 | 0 | 1 | 0 | 0 | 1 | 0 | 0 | 0 |
| S. arizona | | | | | | | | | | | |
| diphasic | 11 | 11 | 11 | 11 | 11 | 11 | 1 | 3 | 0 | 0 | 4 |
| monophasic | 30 | 30 | 30 | 30 | 30 | 30 | 0 | 0 | 0 | 0 | 23 |

*Number of isolates giving a positive result are listed.

Clones RF356, RF352, RF354, and RF355-1, like RF305-1, hybridize to all Salmonella isolates (clone RF305, deposited in the ATCC, has since been renamed RF305-1). Clones RF321, RF352, RF354, and RF355-1 are found to contain identical inserts, although at least three are independent clones. RF321 and RF354 contain the same Bam HI fragment, although in opposite orientations relative to the plasmid vector. RF355-1 is derived from a clone which contains, in addition, a second Bam HI fragment which is 1.4 KB in size; the orientation of the 5.6 KB fragment is the same as for RF354. RF352 is identical to RF321. Clone RF356 differs from the others by size and restriction map.

Clones RF319, RF333, RF326, and RF305-1 hybridize to fewer than 100% of all Salmonella isolates surveyed. By size, restriction enzyme map, and hybridization pattern, clones RF333 and RF326 are identical, except that they have opposite orientations in the plasmid vector.

Five of the fragments illustrated in FIG. 2 were deposited in the Agricultural Research Culture Collection (NRRL), International Depository Authority, Peoria, IL, on June 29, 1983. Each fragment is contained in plasmid YEp13, contained in E. coli. The NRRL identifying numbers of the fragments are as follows:

RF 356: NRRL B-15484;
RF 333: NRRL B-15473;
RF 319: NRRL B-15472;
RF 305: NRRL B-15479;
RF 321: NRRL B-15480.

Clones RF304, RF344, RF318, RF347-3, and RF367 hybridize to 50% or less of all Salmonella isolates tested, and are thus much less suitable as probes than the probes of FIG. 2, which are almost certainly chromosomal, consisting of a portion less than the entire chromosome. For RF344 and RF347-3, the hybridization patterns are different from each other. RF318 has the same distribution as RF 347-3, but differs in size and restriction map. Clones RF304 and RF367 have narrow distribution in the genus. However, the hybridization patterns for these two clones are different. All of these clones hybridize to DNA from DB9000, an S. typhimurium LT2 strain which lacks the cryptic plasmid typically found in S. typhimurium. Because the distribution of these cloned fragments varies extensively, RF304, RF344, and RF347-3 may be parts of different phages or plasmids; if so, RF318 and RF347-3 are probably derived from the same plasmid or bacteriophage.

Quantititive Salmonella Detection

Before describing in detail a method for using the probes of the invention to detect Salmonella, it must be pointed out that detection of the hybrid complexes formed betweeen the probes of the invention and Salmonella DNA can be accomplished in a variety of ways. One method is to label the probes, so that the hybrid complexes will also be labeled. The probes can be labeled in any of a variety of ways. Some labeling methods are direct, i.e., the label which is bonded to the probe is itself detectable; examples are radioactive isotopes. Other labels are indirect, i.e., the label is not itself detectable until it undergoes one or more reactions following hybridization; an example is a compound such as biotin, a label which is not itself detectable, but becomes detectable after it reacts with avidin bound to a detectable chemical entity such as a fluorophore, or an enzyme such as horseradish peroxidase (HRP). In the case of HRP, detection is accomplished via a substrate for HRP; a preferred such substrate is the chromogen diaminobenzidine.

For convenience, then, the term "label" as used herein refers to directly detectable entities such as raoioactive isotopes, as well as to indirectly detectable entities such as biotin. The entity, e.g., HRP/avidin, to which an indirectly detectable label bonds to become detectable is referred to herein as an "indicator".

The most preferred labels for the probes are non-isotopic labels attached to the cytosine and adenine bases of the probes via linking groups. Such labeling is described in Landes U.S. Ser. No. 529,044 entitled "Labeled DNA", filed on the same day as this application, assigned to the same assignee as this application, hereby incorporated by reference.

The method of non-isotopic labeling described in the above Landes Pat. Appln. requires that a cross-linking reagent be used to join an enzyme molecule to the DNA; for this reaction to be carried out, the DNA must be in single stranded form. It is convenient, if this type of labeling is to be used, to maintain the probe in single stranded form, prior to labeling. This can be done by incorporating the single stranded probe into a phage vector, e.g. the publicly available phage vector Fd., described in Zindr et al. (1982) Gene 19, 1, using the method described therein, which involves adding Hind III linkers to the ends of a probe and then cloning the probe into the unique Hind III site of phage vector Fd. When the single stranded probe is to be labeled it is cut out of Fd. using Hind III restriction enzyme.

If the probes are to be isotopically labeled, they can conveniently be maintained in a plasmid vector, e.g. YEp13, prior to labeling. Labeling most conveniently involves cutting out of the plasmid the probe to be used in the hybridization assay and then nick-translating the probe. Alternatively, the entire plasmid can be nick-translated and used in the assay. In either case, the probe, which in the plasmid is double-stranded, must first be rendered single-stranded, e.g., by heat treatment or by treatment with a base.

Another detection method, which does not require the labeling of the probe, is the so-called sandwich hybridization technique, described in European Pat. Appln. No. 0079139, hereby incorporated by reference. In this assay, an unlabeled probe, contained in a single-stranded vector, hybridizes to Salmonella DNA, and a labeled, single-stranded vector, not containing the probe, hybridizes to the probe-containing vector, labeling the whole hybrid complex.

Any of the Salmonella-specific probes of the invention, labeled with, e.g., $^{32}P$, are used to demonstrate the presence of Salmonella in a mixture of bacteria, as follows. A pure culture of *S. typhimurium* is serially diluted and then spotted onto a series of nitrocellulose membranes. A parallel set of membranes is spotted with the same serial dilutions of *S. typhimurium*, each of which is mixed with a constant amount of *E. coli*. The bacteria are lysed and their DNA denatured, e.g. by immersion of the membranes in NaOH/NaCl, and the denaturing solution neutralized, e.g. by a second immersion in Tris/NaCl. The bacterial DNA is then fixed onto the membranes by immersing the membranes in absolute ethanol and then allowing them to dry. The membranes are then soaked at 37° C. for 2 hr. in prehybridization solution, as described in Denhardt (1966) BBRC 23, 641. The prehybridization solution consists of 45% formamide, 25 mM Na pH 6.8, 5 X Denhardt's solution (1 X is 0.02%, w/v, of polyvinyl pyrolidone, Ficoll 500, and bovine serum albumin), and 250 ug/ml sonicated, denatured carrier DNA (from, e.g., calf thymus or salmon sperm). Hybridization is then carried out, with one or more of the DNA probes described above, using a conventional hybridization technique such as that described in Grunstein et al. (1975) PNAS USA 72, 3961 or Falkow et al. U.S. Pat. No. 4,358,535, hereby incorporated by reference. The hybridization solution has the same composition as the prehybridization solution, above, except that it further contains 10%, w/v, dextran sulfate and 0.1–10 ug/ml labeled probe.

The hybridization reaction is allowed to proceed for 2 hrs. at 37° C. Non-hybridized probe is then removed by repetitive washes of the solid support with an established wash regimen, e.g., 3 washes of 10 minutes each with 10 mM NaCl at 37° C.

Labeled DNA complexes fixed to the membranes quantitatively correspond to the amount of Salmonella on each membrane. For each dilution, the same quantitative result is obtained for the pure Salmonella samples as for those containing. *E. coli*, demonstrating that the presence of *E. coli* DNA does not affect the hybridization of the probe to the Salmonella DNA present, and that the Salmonella specific probes of the invention can be used to detect the presence of Salmonella in a mixture of bacteria.

Although good results can be obtained using only one of the probes of the invention, we have found, as discussed above, that best results are obtained using more than one different probe at the same time.

Detection of Salmonella in Food

The procedure for detecting the presence of Salmonella in food can be summarized as follows.

Fifteen 25-gram randomly selected samples of food to be tested are cultured in nutrient broth for 20–24 hours at 30–37° C. Referring to FIG. 1, a one ml aliquot of the culture is then pipetted into cylindrical portion 14 and a vacuum applied, as described above, so that small Salmonella-sized bacteria are collected on nitrocellulose filter 26; portion 14, containing food and large bacteria, is then discarded.

Next, a solution, e.g. NaOH/NaCl, which is capable of both lysing bacteria and denaturing bacterial DNA, is added to portion 16. Following denaturation, Tris/NaCl is added to neutralize the NaOH/NaCl.

The bacterial DNA is then fixed onto membrane 26 by adding absolute ethanol to the membrane and then allowing it to dry, as described in Groet et al. U.S. Pat. Appln. Ser. No. 448,979, filed on Dec. 13, 1982, assigned to the same assignee as this application, hereby incorporated by reference.

Following fixation, membrane 26 is soaked for 15–30 min. in pre-hybridization buffer, described above. Hybridization buffer, containing $^{32}P$-labeled probe, is then added, as described above, and hybridization is allowed to proceed for 2–3 hrs. at 37° C. Radioactive hybrid DNA complexes indicate the presence in the food sample of Salmonella.

The above procedure can be used to detect the presence of Salmonella in any foods, including all of the foods listed in Table 2.

The processing of the food samples prior to the hybridization assay is carried out according to the methods described by the Food and Drug Administration in U.S. FDA, Bureau of Foods, Div. of Microbiol. (1978) Bacterialog. Anal. Manual, 5th Ed., Wash., D.C. Association of Anal. Chem.

As indicated in Table 2, some of the food cultures tested were inoculated with predetermined numbers of Salmonella prior to the overnight incubation. In those cases, Salmonella cultures were grown to approximately $2\times10^8$ cells/ml in L broth, diluted in L broth, and added to the food cultures.

All five of the NRRL-deposited probes, nick-translated with $^{32}$P, were used to assay, using nucleic acid hybridization, the following foods (samples of food tested were both those which had been inoculated with Salmonella, and uncontaminated samples): peanut butter, soy flour, macaroni, chocolate pieces, nonfat dry milk, thawed frozen fish sticks, dried eggs, dog treats, sour cream, and instant mashed potatoes.

Inocdated samples of each type of food give very strong hybridization results, while uncontaminated samples give very clean negative results.

To determine whether different Salmonella strains commonly found in food behave similarly in hybridization assays, soy flour cultures are inoculated with about 1,000 organisms of four of the Salmonella strains most commonly found in food, human clinical samples, and other animals, according to the 1980 Salmonella Surveillance Annual Summary of the Center for Disease Control, issued December, 1982. These four strains are *S. typhimurium; S. derby; S. heidelberg,* and *S. st paul.* The soy cultures are incubated overnight. Replicate filters are prepared from each culture and assayed using the five NRRL-deposited probes, nick-translated with $^{32}$P. The filters are exposed to film for autoradiography and later counted in a scintillation counter.

Some strains of Salmonella (e.g., *S. heidelberg*) may behave differently in the hybridization assay to the extent that the intensity of hybridization is less than that for an equal number of Salmonella of another strain. However, this difference does not appear to be probe-dependent, and the difference may result from some mechanical phenomenon such as inadequate lysis of the bacteria on the filters, causing less DNA to be exposed during the hybridization reaction. Differences may be diminished by using a greater amount of probe DNA in the assays. Despite this lower hybridization intensity, *S. heidelberg* can be easily detected in this assay using any or all of the Salmonella-specific probes.

Thus diverse food types can be handled with ease in this test. An overnight period of incubation of these foods in nutrient broth is desirable, but selective enrichment is not required.

The advantages of this system are multifold. The time required for the analysis of a single food sample is greatly reduced from the 5-7 days currently required for a microbiological assay. In addition, a larger number of food samples can be processed in a small period of time. In these studies the background hybridization is quite low, which makes possible a clear distinction between positive and negative results. The probes described herein can also be applied in a clinical setting to test for the presence of Salmonella in stools; stool samples can be processed in the same way as food samples.

Other Embodiments

Other embodiments are within the following claims. For example, as has been mentioned, probes can be labeled using a variety of labels. Nitrocellulose membranes are preferred for binding DNA, but any suitable DNA-binding support, e.g. diazobenzyloxymethyl paper, can be used.

What is claimed is:

1. A method of detecting the presence of Salmonella in a bacteria-containing sample comprising
   providing a sample suspected of containing Salmonella,
   lysing the bacteria in said sample to release their DNA,
   denaturing said released DNA,
   providing at least one DNA probe which is capable of stably hybridizing to DNA from 80% or more of Salmonella species, and not to DNA of any other enterobacteria, to form detectable complexes,
   contacting said DNA probe with said released DNA in said sample under conditions which allow said probe to hydridize to Salmonella DNA present in said sample to form hybrid DNA complexes, and
   detecting said hybrid DNA complexes as an indication of the presence in said sample of Salmonella.

2. The method of claim 1 wherein said probe is labeled.

3. The method of claim 2 wherein said label is either capable of being detected or is capable of selectively bonding to an indicator to form a detectable complex.

4. The method of claim 3 wherein said probe is labeled with a radioactive isotope.

5. The method of claim 4 wherein said radioactive isotope is $^{32}$P which has been incorporated into said probe by nick-translation.

6. The method of claim 4 wherein said radioactive isotope is $^{125}$I which has been incorporated into said probe by nick-translation.

7. The method of claim 3 wherein said label is biotin and said indicator is avidin to which is bonded a chemical entity which, when said avidin is bonded to said biotin on said hybrid DNA complex, is capable of being detected.

8. The method of claim 7 wherein said chemical entity is a fluorophore which renders said hybrid DNA complexes fluorometrically detectable.

9. The method of claim 7 wherein said chemical entity is an electron-dense compound which renders said hybrid DNA complexes detectable by an electron microscope.

10. The method of claim 7 wherein said chemical entity is an antibody which renders said hybrid DNA complexes immunologically detectable.

11. The method of claim 7 wherein said chemical entity is one of a catalyst/substrate pair which renders said hybrid DNA complexes enzymatically detectable.

12. The method of claim 1 wherein, prior to contacting said DNA with said probe, said bacteria are separated out of said sample and said DNA is immobilized on a DNA binding support.

13. The method of claim 12 wherein said support is a nitrocellulose membrane.

14. The method of claim 1, wherein said probe is unlabeled and said detection of hybrid DNA complexes is carried out by sandwich hybridization.

15. The method of claim 1, employing at least 2 different said probes

16. The method of claim 15, employing at least 3 different said probes.

17. The method of claim 16, employing at least 4 different said probes

18. The method of claim 17, employing at least 5 different said probes.

19. A DNA probe consisting of a portion of a Salmonella chromosome which is capable of stably hybridizing to DNA from 80% or more of Salmonella species and not to other enterobacteria.

20. The DNA probe of claim 19 wherein said probe is labeled.

21. The DNA probe of claim 19 wherein said probe is capable of stably hybridizing to 90% or more of Salmonella species.

22. The DNA probe of claim 19, said probe being the Salmonella DNA BamHl fragment contained in plasmid YEp13 contained in *E. coli,* said plasmid-containing *E. coli* being NRRL B-15480.

23. The DNA probe of claim 19, said probe being the Salmonella DNA BamHl fragment contained in plasmid YEp13 contained in *E. coil,* said plasmid-containing *E. coli* being NRRL B-15479, ATCC 39261.

24. The DNA probe of claim 19, said probe being the *Salmonella* DNA *BamHl* fragment contained in plasmid YEp13 contained in *E. coli,* said plasmid-containing *E. coli* being NRRL B-15472.

25. The DNA probe of claim 19, said probe being the *Salmonella* DNA *BamHl* fragment contained in plasmid YEp13 contained in *E. coli,* said plasmid-containing *E. coli* being NRRL B-15473.

26. The DNA probe of claim 19, said probe being the *Salmonella* DNA *BamHl* fragment contained in plasmid YE13 contained in *E. coli,* said plasmid-containing *E. coli* being NRRL B-15484.

* * * * *

UNITED STATES PATENT AND TRADEMARK OFFICE
CERTIFICATE OF CORRECTION

PATENT NO. : 4,689,295

DATED : August 25, 1987

INVENTOR(S) : Taber, et al

It is certified that error appears in the above-identified patent and that said Letters Patent is hereby corrected as shown below:

Columns 9 and 10, in Table 2, replace "0" in line "S. new brunswick" and column "RF305-1" with --3--; and in line "S. quimbamba" and column "RF304", replace " " with --0--.

In column 12, line 68, replace "raoioactive" with --radioactive--.

In column 13, line 21, replace "Zindr" with --Zinder--; on line 63, replace "Na" with --Na$_2$PO$_4$--.

In column 15, line 11, replace "Inocdated", with --Inoculated--.

In claims 22 and 23, second lines, replace "BamHI" with --BamHI--, and replace "Salmonella" with --Salmonella--

In claims 24-26, second lines, replace "BamH1" with --BamH1--.

Signed and Sealed this

Twenty-sixth Day of February, 1991

Attest:

HARRY F. MANBECK, JR.

Attesting Officer     Commissioner of Patents and Trademarks